US00PP29878P2

(12) United States Plant Patent
Bedard et al.

(10) Patent No.: US PP29,878 P2
(45) Date of Patent: Nov. 27, 2018

(54) FLORIBUNDA ROSE PLANT NAMED 'WEKCIFRABAUN'

(50) Latin Name: *Rosa hybrida*
Varietal Denomination: WEKcifrabaun

(71) Applicant: Early Morning LLC, Lawrenceburg, IN (US)

(72) Inventors: Christian Bedard, Placentia, CA (US); Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 15/732,576

(22) Filed: Nov. 29, 2017

(51) Int. Cl.
*A01H 5/02* (2018.01)

(52) U.S. Cl.
USPC ..... Plt./143

(58) Field of Classification Search
USPC ..... Plt./143
See application file for complete search history.

(56) References Cited

U.S. PATENT DOCUMENTS

PP10,126 P 11/1997 Carruth

*Primary Examiner* — Annette H Para
(74) *Attorney, Agent, or Firm* — McKee, Voorhees & Sease, PLC

(57) ABSTRACT

A new variety of Floribunda rose suitable for garden decoration, having flowers of scarlet red striped gold coloration.

1 Drawing Sheet

Classification: The present invention relates to a new *Rosa hybrida* plant.

Variety denomination: The new plant has the varietal denomination 'WEKcifrabaun'.

BACKGROUND OF THE INVENTION

This invention relates to a new and distinct variety of Floribunda Rose. It has a non-disseminated seedling of our creation as its seed parent with the following genetic origin (City of San Francisco x Baby Love) and an unknown pollen parent.

SUMMARY OF THE INVENTION

Among the features which distinguish the new variety from other presently available and commercial rose cultivars known to the inventor are the following combinations of characteristics: its unique scarlet red striped gold flower coloration, its many stipitate glands and numerous hairs on the surface of the bud and its numerous hairs on the upper side and under side of the rachis. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKcifrabaun' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKcifrabaun' bears double flowers (about 20 to 31 petals) of scarlet red striped gold coloration, the non-disseminated seedling bears double flowers of medium red coloration with significantly lesser petalage (about 15 to 20 petals). The new variety has an upright moderately spreading medium height growing habit (about 110 to about 170 cm. in height), whereas the seed parent has an upright bushy significantly shorter growing habit (about 90 cm. in height).

The pollen parent is unknown.

COMPARISON WITH THE CLOSEST COMMERCIALLY AVAILABLE CULTIVAR

The new variety may be distinguished from its closest commercially available cultivar, 'WEKplapep' (U.S. Plant Pat. No. 10,126) by the following combination of characteristics:

whereas 'WEKcifrabaun' bears double flowers (about 20 to 31 petals) of scarlet red striped gold coloration, 'WEKplapep' bears double flowers of striped red and white coloration with significantly heavier petalage (about 31 to 36 petals). The new variety has a slight fruity fragrance, whereas the closest commercially available cultivar has a strong damask and spicy fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, sometimes in clusters of two to five or more per stem. Flowers may be borne in regular rounded clusters on strong short to medium length stems (about 18 to about 48 cm.). The cluster ranges from about 12.5 to about 25.0 cm. in diameter. Outdoors, the plant blooms abundantly and nearly continuously during the growing season. The flowers have a slight fruity fragrance.

BUD

The peduncle is about 3.1 to about 7.2 cm. in length, of average caliper (about 0.2 to about 0.3 cm. in diameter), and usually erect to somewhat stiff. It is moderately rough, with few stipitate glands, and some hairs. Peduncle color is between 144A and 146B often heavily suffused, especially on the side exposed to the sun, with between 187B and 187A.

Before the calyx breaks, the bud is about 1.2 to about 1.7 cm. in diameter at the widest point, about 1.5 to about 1.9 cm. in length, and pointed to somewhat ovoid in shape. The surface of the bud bears between 5 to 9 foliaceous appendages with many stipitate glands and numerous hairs, usually with slender entire foliaceous parts extending beyond the tip of the bud about ¾ or more of its length. Bud color is between 137B and 137C often heavily suffused, especially on the side exposed to the sun, with between 187B and 187A.

The sepals are 5 per flower, about 2.0 to about 3.6 cm. in length and about 0.7 to about 1.1 cm. in width at the widest point. The outer surface color of the sepal is between 137B and 137C often heavily suffused, especially on the side exposed to the sun, with between 187B and 187A. The outer surface of the sepal is somewhat rough and bears between 0 to 6 foliaceous appendages with many stipitate glands and numerous hairs. The inner surface color of the sepal is near 146D broadly bordered by near 137B. After the sepals open, the inner surface color is often heavily suffused, especially on the area exposed to the sun, with between 187A and 187B. The inner surface of the sepal is covered with fine wooly tomentum; sepal margins are entire and lined with few stipitate glands and numerous hairs. The sepals are moderately permanent, and usually straight in shape with acute apices.

The receptacle of the flower is of medium length (about 0.5 to about 0.7 cm.) and average in caliper (about 0.7 to about 0.8 cm. in diameter). The receptacle is urn-shaped in form. Its surface is smooth with few hairs and very few stipitate glands and with moderately thin fleshy walls. The receptacle color is between 144A and 146A often moderately suffused, especially on the side exposed to the sun, with between 187B and 187A.

As the petals open (after the calyx breaks), the bud is about 1.4 to about 2.3 cm. in diameter at the widest point, about 1.7 to about 3.1 cm. in length, and moderately ovoid to somewhat pointed in form. The color of the under surfaces of the newly opened petals is irregularly striped and flecked with as dark as between 187B and 53A to as light as between 11A and 10A sometimes lightly suffused with between 53B and 60A. At the point where the petal attaches, there is a moderately small zone of between 3C and 4B. The color of the upper surfaces of the newly opened petals is irregularly striped and flecked with as dark as near 53A to as light as between 34A and 42B. At the point where the petal attaches, there is a moderately small zone of between 2B and 1A.

BLOOM

When fully open, the bloom ranges from about 7.5 to about 10.8 cm. in diameter. Petalage is double with about 20 to 31 petals and about 2 to 5 petaloids irregularly arranged. When partially open, the bloom form is moderately cupped to somewhat high centered, and the petals are moderately loosely spiraled to cupped with petal edges somewhat reflexed outward. When fully open, the bloom form is cupped to somewhat flat, and the petals are loosely cupped to slightly undulated with petal edges moderately reflexed outward.

PETALS

The substance of the petals is moderately heavy and of medium thickness, with upper surfaces slightly satiny and under surfaces slightly shiny. The petals are about 2.9 to about 4.8 cm. in length and about 2.3 to about 4.3 cm. in width at the widest point. Petal margins are entire.

The outer petals are moderately obovate to somewhat rounded in shape with rounded apices.

The inner petals are broadly obovate in shape with rounded apices.

Petaloids are about 0.9 to about 3.3 cm. in length and about 0.7 to about 1.7 cm. in width at the widest point. Petaloids are irregularly shaped somewhat oblanceolate with rounded apices.

NEWLY OPENED FLOWER

The under surface color of the outer petals is irregularly striped and flecked with as dark as between 53B and 53C to as light as between 20D and 18C. At the point where the petal attaches, there is a somewhat large zone of between 2C and 3D. The upper surface color of the outer petals is irregularly striped and flecked with as dark as between 53C and 50B to as light as between 20C and 19B sometimes lightly suffused with between 53B and 50C. At the point where the petal attaches, there is a somewhat large zone of between 5C and 4B.

The under surface color of the intermediate and inner petals is irregularly striped and flecked with as dark as between 47B and 47C to as light as between 12D and 20C. The upper surface color of the intermediate and inner petals is irregularly striped and flecked with as dark as between 47C and 47D to as light as between 20C and 18D.

The under and upper surface colors of the petaloids are similar in coloration to the upper and under surfaces of the intermediate and inner petals.

The general tonality of the newly opened flower is irregularly striped and flecked with as dark as between 47C and 47D to as light as between 20C and 18D.

THREE-DAY-OLD FLOWER

The under surface color of the outer petals is irregularly striped and flecked with as dark as between 53C and 53D to as light as between 20D and 18C. At the point where the petal attaches, there is a somewhat large zone of between 4D and 2D. The upper surface color of the outer petals is irregularly striped and flecked with as dark as between 53C and 50B to as light as between 20C and 19B sometimes lightly suffused with between 53B and 50C. At the point where the petal attaches, there is a somewhat large zone of between 4C and 2D.

The under surface color of the intermediate and inner petals is irregularly striped and flecked with as dark as between 53C and 53D to as light as between 20D and 18C. The upper surface color of the intermediate and inner petals is irregularly striped and flecked with as dark as between 52A and 50B to as light as between 20C and 19B sometimes lightly suffused with between 53B and 50C.

The under and upper surface colors of the petaloids are similar in coloration to the upper and under surfaces of the intermediate and inner petals.

The general tonality of the three-day-old flower is irregularly striped and flecked with as dark as between 52A and 50B to as light as between 20C and 19B sometimes lightly suffused with between 53B and 50C.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 140) and are arranged regularly about the pistils; a few are mixed with petaloids. The filaments are of moderately short to medium length (about 0.4 to about 0.9 cm.) most with anthers. Filaments are between 13B and 12A in color sometimes lightly suffused with between 53C and 53B. The anthers are somewhat small for the class and all open approximately at the same time. Anther color when immature is near 21B on the external part and near 13D on the internal part. Anther color at maturity is near 163A on the external part and near 200A on the internal part. Pollen is moderate and between 18B and 16D in color.

FEMALE REPRODUCTIVE ORGANS

Pistils vary in number (average about 55). The styles are moderately even, somewhat long in length (about 0.6 to about 0.8 cm.), moderately heavy in caliper, and loosely bunched. Stigma color is near 16D. Style color is between 149D and 145D sometimes lightly suffused near the top with near 53B. Ovaries are usually all enclosed in the calyx. The ovaries are of small size and between 158A and 158B in color.

Hips are of somewhat short length (about 1.0 to about 1.7 cm.), rounded in form with a flat top, and between 34B and 34A in color when ripe. The hip surface is smooth with thick fleshy walls.

The seeds are irregularly rounded, smooth in texture, approximately 5 to about 11 per hip, about 0.4 to about 0.7 cm. in diameter at the widest point and between 165D and 164D in color.

FOLIAGE

The compound leaves are usually comprised of three to seven leaflets and are borne abundantly. The five-leaflet leaves are about 8.0 to about 16.7 cm. in length and about 6.0 to about 11.7 cm. in width at the widest point, moderately leathery to somewhat crisp in texture on both sides, and glossy in finish on the upper side and somewhat glossy in finish on the underside. The leaves have a pinnate venation pattern. The terminal leaflets are about 3.7 to about 7.1 cm. in length and about 2.5 to about 4.4 cm. in width at the widest point, shaped moderately oval to somewhat ovate with acute apices and rounded bases. Their margins are usually simply serrate.

The upper surface color of the mature leaf is between 139A and 137A. The under surface color of the mature leaf is between 147B and 137C. The under and upper colors of the leaf veins on the mature leaf are similar in coloration to the upper and under surfaces colors of the mature leaf. The upper surface color of the young leaf is between 137B and 137A, often heavily suffused with between 187A and 187B. The under surface color of the young leaf is between 138B and 137C, often moderately suffused with between 187A and 187B. The under and upper colors of the leaf veins on the young leaf are similar in coloration to the upper and under surfaces colors of the young leaf.

The rachis is about 3.0 to about 7.9 cm. in length and about 0.1 to about 0.15 cm in width at the widest point, and rough. The upper side is deeply grooved with numerous hairs and few stipitate glands on the edges of the grooves. The under side of the rachis is rough with numerous hairs, few stipitate glands and small prickles. The rachis color is near 146C on the underside and near 137C on the upper side, often heavily suffused on the young leaves with between 187A and 187B.

The stipules are about 1.2 to about 1.6 cm. in length and of medium width (about 0.4 to about 0.8 cm.) with moderately short straight points that usually turn out at an angle of more than 45 degrees and sometimes recurve toward the stem. The under and upper surface color of the stipule is between 137A and 139A. The upper and under surfaces of the stipules are smooth in texture.

The petiole is somewhat light to average in caliper and rough. The upper side is deeply grooved with numerous hairs and few stipitate glands on the edges of the grooves. The under side of the petiole is rough with numerous hairs, few stipitate glands and small prickles. The petiole is about 0.2 to about 1.5 cm. in length and about 0.1 to about 0.15 cm in width at the widest point. The petiole color is near 146C on the underside and near 137C on the upper side, often heavily suffused on the young leaves with between 187A and 187B.

The plant displays an above average degree of resistance to powdery mildew (Sphaerotheca pannosa), downy mildew (Peronospora sparsa), and rust (Phragmidium sp.) as compared to other commercial varieties grown under comparable conditions in Pomona, Calif. The plant's winter hardiness and drought/heat tolerance are yet to be determined.

GROWTH

The plant has an upright moderately spreading medium height growing habit (about 110 to about 170 cm. in height and about 80 to about 130 cm. spread at the widest point), with full branching. It displays vigorous growth and the canes are of moderately heavy to medium size caliper for the class (about 1.9 to about 3.5 cm. in diameter at the widest point).

The color of the major stems is between 147B and 146B. The major stems are rough in texture and they bear many large prickles that are about 0.8 to about 1.2 cm. in length. The large prickles are angled slightly downward with a long broad oval base; prickle color is between 165A and 200D often moderately suffused with near 201B. The major stem bears some small prickles of similar shape and coloration.

The color of the branches is between 137C and 146B. The branches are rough in texture and they bear some large prickles which are of similar shape to the large prickles on the major stems. The prickles are about 0.4 to about 0.7 cm. in length. Prickle color is near 152D sometimes lightly suffused with near 187D. The branches bear some small prickles of similar shape and coloration.

The color of the new shoots is between 146C and 146B sometimes moderately suffused with between 187B and 187C. The new shoots are rough in texture and they bear few large prickles which are of similar size and shape to the large prickles on the branches; prickle color is between 146D and 146C sometimes lightly suffused with near 187D. The shoots bear few small prickles of similar shape and coloration.

I claim:

1. A new and distinct Floribunda rose plant of the variety substantially as described and illustrated herein.

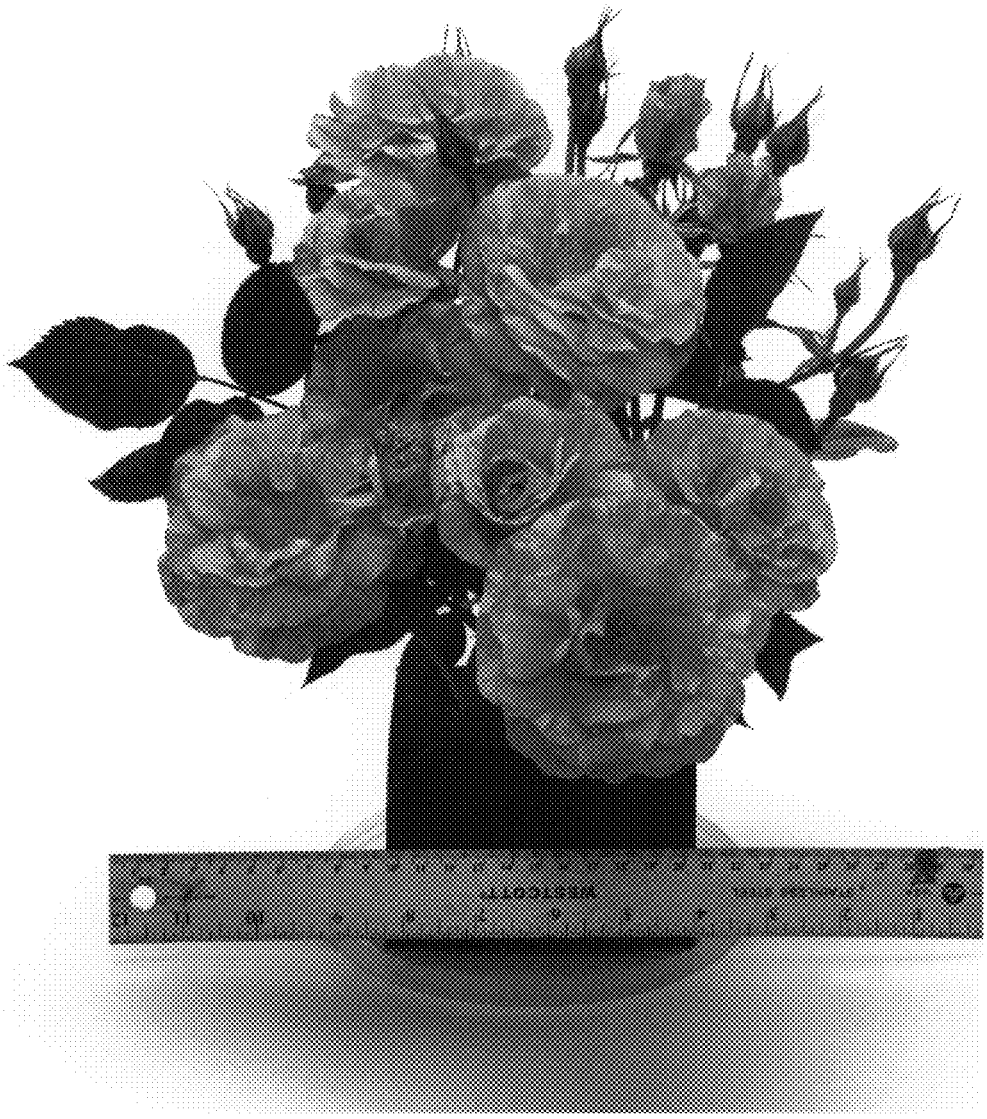

* * * * *